(12) United States Patent
Litvak et al.

(10) Patent No.: US 8,498,714 B2
(45) Date of Patent: Jul. 30, 2013

(54) METHODS AND SYSTEMS OF CONVEYING FINE STRUCTURE INFORMATION TO A COCHLEAR IMPLANT PATIENT

(75) Inventors: Leonid M. Litvak, Los Angeles, CA (US); Aniket Saoji, Northridge, CA (US); Anthony J. Spahr, Litchfield Park, AZ (US); Edward Overstreet, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 924 days.

(21) Appl. No.: 12/559,759

(22) Filed: Sep. 15, 2009

(65) Prior Publication Data
US 2010/0070000 A1    Mar. 18, 2010

Related U.S. Application Data

(60) Provisional application No. 61/098,153, filed on Sep. 18, 2008.

(51) Int. Cl.
*A61N 1/18* (2006.01)

(52) U.S. Cl.
USPC ....... 607/55; 607/2; 607/56; 607/57; 607/137

(58) Field of Classification Search
USPC .................................. 607/2, 55, 56, 57, 137
See application file for complete search history.

(56) References Cited

U.S. PATENT DOCUMENTS

| | | | |
|---|---|---|---|
| 6,594,525 B1 * | 7/2003 | Zierhofer | 607/57 |
| 7,225,027 B2 | 5/2007 | Zeng et al. | |
| 7,231,257 B2 | 6/2007 | McDermott et al. | |
| 7,251,530 B1 * | 7/2007 | Overstreet et al. | 607/55 |
| 2003/0105504 A1 * | 6/2003 | Zierhofer | 607/74 |
| 2003/0167077 A1 * | 9/2003 | Blamey et al. | 607/57 |
| 2009/0018614 A1 * | 1/2009 | Zierhofer | 607/56 |
| 2009/0254150 A1 * | 10/2009 | Zierhofer | 607/57 |
| 2009/0264960 A1 * | 10/2009 | Litvak et al. | 607/57 |

FOREIGN PATENT DOCUMENTS

| | | |
|---|---|---|
| WO | WO-01/13991 | 3/2001 |
| WO | WO 2009/001251 | 1/2009 |

OTHER PUBLICATIONS

Litvak, et al., "Improved temporal coding of sinusoids in electric stimulation of the auditory nerve using desynchronizing pulse trains", *Journal of the Acoustical Society of America*, vol. 114, No. 4, Oct. 1, 2003.

Smith, et al., "Chimaeric sounds reveal dichotomies in auditory perception", *Nature, Nature Publishing Group*, London, UK, vol. 416, No. 6876, Mar. 17, 2002

(Continued)

*Primary Examiner* — Niketa Patel
*Assistant Examiner* — Christopher A Flory
(74) *Attorney, Agent, or Firm* — ALG Intellectual Property, LLC

(57) ABSTRACT

An exemplary method of conveying fine structure information to a cochlear implant patient includes dividing an audio signal into a plurality of analysis channels, generating electrical stimulation in accordance with the information contained within each of the analysis channels, applying the electrical stimulation to at least one stimulation site within a patient via a plurality of stimulation channels, and at least partially isolating one of the stimulation channels from a rest of the stimulation channels, wherein fine structure information is conveyed to the patient via the isolated stimulation channel. Corresponding methods and systems are also disclosed.

5 Claims, 9 Drawing Sheets

OTHER PUBLICATIONS

Majdak, et al., "Effects of interaural time differences in fine structure and envelope on lateral discrimination in electric hearing", *Journal of the Acoustical Society of America*, vol. 120, No. 4, Oct. 1, 2006.

International Search Report and Written Opinion received in International Application No. PCT/US2009/056926, Nov. 5, 2009.

* cited by examiner

METHODS AND SYSTEMS OF CONVEYING FINE STRUCTURE INFORMATION TO A COCHLEAR IMPLANT PATIENT

RELATED APPLICATIONS

The present application claims priority under 35 U.S.C. §119(e) to U.S. Provisional Patent Application No. 61/098, 153 by Leonid M. Litvak et al., filed on Sep. 18, 2008, and entitled "Methods and Systems of Conveying Fine Structure Information to a Cochlear Implant Patient," the contents of which are hereby incorporated by reference in their entirety.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels. However, in traditional cochlear implants, important information from an audio signal can be lost during translation of the audio signal into electrical stimulation pulses. Such losses during translation may make it difficult for cochlear implant patients to enjoy the full advantages of unmitigated hearing. For example, losses during translation may make it difficult for cochlear implant patients to identify a speaker, understand speech, and appreciate the nuances of musical sound.

Studies suggest, however, that many advantages of unmitigated hearing can be obtained by hearing impaired individuals with enough residual hearing to clearly perceive, either naturally or with the aid of an amplification device, pitch and other fine structure information in the lower frequency ranges of audible sound. These studies, for example, show that clear perception of such fine structure information may improve performance in the above mentioned skills of speaker identification, speech recognition, and musical perception. Unfortunately, fine structure information is often lost, distorted, or otherwise adversely affected by traditional cochlear implants.

SUMMARY

Methods of conveying fine structure information to a cochlear implant patient include dividing an audio signal into a plurality of analysis channels corresponding to distinct frequency bands, with one of the analysis channels containing fine structure information corresponding to the audio signal. The methods further include generating electrical stimulation in accordance with information within each of the analysis channels and applying the electrical stimulation to at least one stimulation site within a patient via a plurality of stimulation channels corresponding to the analysis channels. Additionally, the methods include at least partially isolating the stimulation channel conveying fine structure information from the rest of the stimulation channels.

Systems for conveying fine structure information to a cochlear implant patient include a sound processor configured to divide an audio signal into a plurality of analysis channels corresponding to distinct frequency bands, with one of the analysis channels containing fine structure information corresponding to the audio signal. Such systems also include an implantable cochlear stimulator communicatively coupled to the sound processor and configured to generate electrical stimulation in accordance with information contained within the analysis channels, apply the electrical stimulation to at least one stimulation site within a patient via a plurality of stimulation channels corresponding to the analysis channels, and at least partially isolate the stimulation channel conveying fine structure information from the rest of the stimulation channels.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems of conveying fine structure information to a cochlear implant patient are described herein. In some examples, a sound processor is configured to divide an audio signal into a plurality of analysis channels containing information corresponding to distinct frequency bands. One of the analysis channels contains fine structure information corresponding to the audio signal. An implantable cochlear stimulator is communicatively coupled to the sound processor and configured to generate electrical stimulation in accordance with information in the analysis channels. The implantable cochlear stimulator is further configured to apply the electrical stimulation to one or more stimulation sites within the patient via a plurality of stimulation channels corresponding to the analysis channels. The implantable cochlear stimulator is further configured to at least partially isolate the stimulation channel conveying the fine structure information from the rest of the stimulation channels. In this manner, the patient may more accurately and effectively perceive the fine structure information contained within the first stimulation channel.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
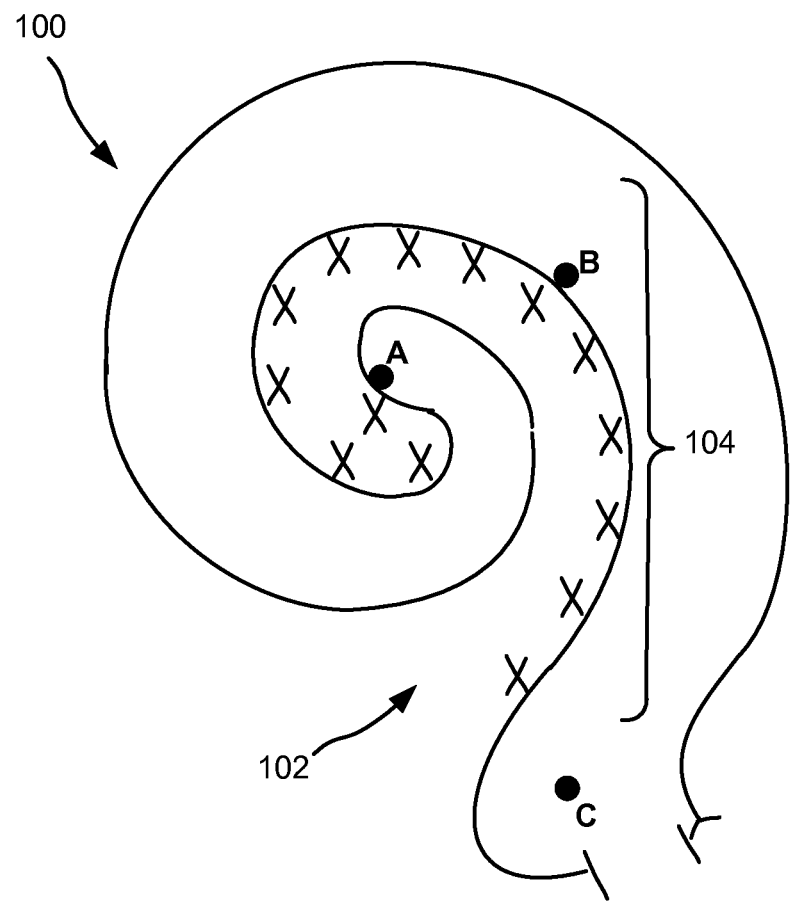
FIG. 1 illustrates a schematic structure of the human cochlea according to principles described herein.

FIG. 1 illustrates a schematic structure of the human cochlea 100. The cochlea 100 includes a duct 102. The section of the cochlea 100 and of the duct 102 from point A to point B, i.e., section AB, has a spiral shape. In contrast, the section from point B to point C, i.e., section BC, is relatively straight.

Within the duct 102 are a number of locations 104, that, when stimulated, convey sound information to the brain. These locations 104 are depicted as Xs in FIG. 1. Each location 104 corresponds to a different perceived audio frequency. For example, stimulation of locations 104 closer to point A causes the patient to perceive relatively low frequencies, while stimulation of locations 104 closer to point C causes the patient to perceive relatively high frequencies. In patients with sensorineural hearing loss, a cochlear implant system can electrically stimulate various locations 104 within the duct 102 to provide a sensation of hearing.

Figure 2:
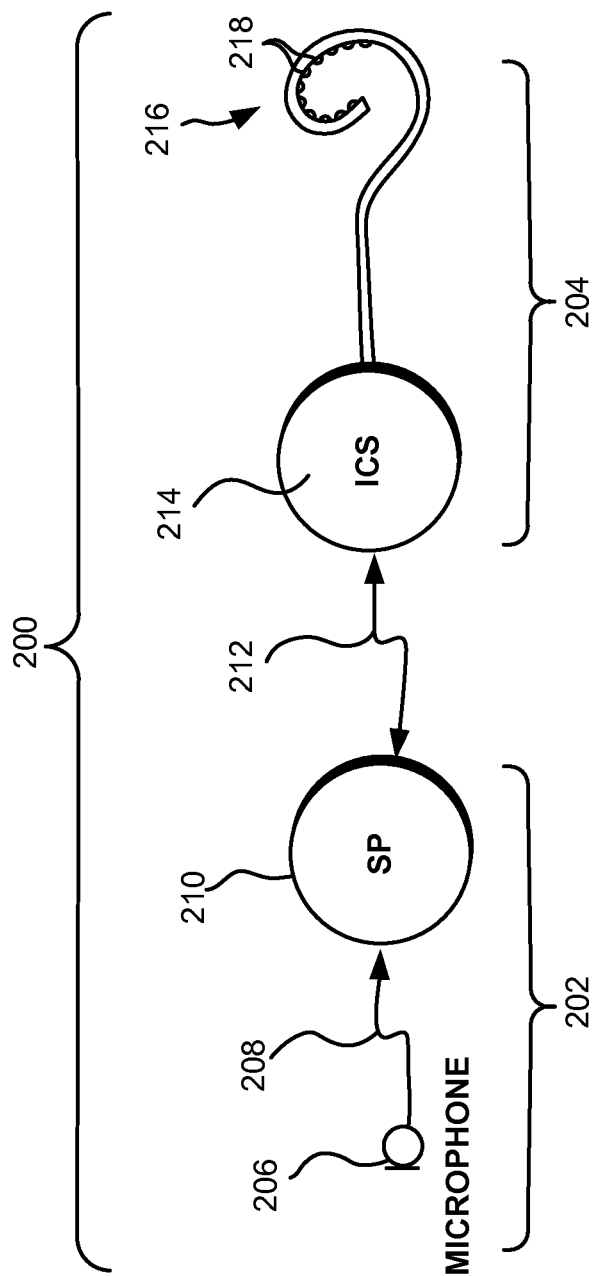
FIG. 2 illustrates an exemplary cochlear implant system according to principles described herein.

FIG. 2 illustrates an exemplary cochlear implant system 200 that may be used in accordance with the present methods and systems. The cochlear implant system 200 of FIG. 2 includes a sound processor portion 202 and a cochlear stimulation portion 204. The sound processor portion 202 may include a sound processor 210, a microphone 206, and/or additional circuitry as best serves a particular application. The cochlear stimulation portion 204 may include an implantable cochlear stimulator 214, a number of electrodes 218 disposed on a lead 216, and/or additional circuitry as best serves a particular application. The components within the sound processor portion 202 and the cochlear stimulation portion 204 will be described in more detail below.

The microphone 206 of FIG. 2 is configured to sense audio signals and convert the sensed signals to corresponding electrical signals. The electrical signals are sent from the microphone 206 to the sound processor 210 via a communication link 208. The microphone 206 may be connected directly to, or integrated with, the sound processor 210.

The sound processor 210 processes these converted audio signals in accordance with a selected sound processing strategy to generate appropriate stimulation parameters for controlling the implantable cochlear stimulator 214. These stimulation parameters may specify or define the polarity, magnitude, location (i.e., which electrode pair or electrode group receive the stimulation current), stimulation rate, timing (i.e., when the stimulation current is to be applied to a particular electrode pair), and/or any other characteristic of the stimulation current that is generated by the implantable cochlear stimulator 214. To facilitate processing of the converted audio signals, sound processor 210 may include any combination of hardware, software, and/or firmware. For example, sound processor 210 may include one or more processors (e.g., digital signal processors), memory having one or more software applications residing therein, and/or any other component as may serve a particular application.

The lead 216 shown in FIG. 2 is configured to be inserted within a duct 102 of the cochlea 100. As shown in FIG. 2, the lead 216 includes a plurality of electrodes 218, e.g., sixteen electrodes, spaced along its length. It will be understood, however, that any number of electrodes 218 may be disposed on the lead 216. As will be described in more detail below, electronic circuitry within the implantable cochlear stimulator 214 is configured to generate and apply stimulation current to one or more stimulation sites within the duct 102 of the cochlea 100 via selected stimulation channels (i.e., pairs or groups of the individual electrodes 218) in accordance with a specified stimulation strategy defined by the sound processor 210.

The implantable cochlear stimulator 214 and the sound processor 210 may be electronically connected via a suitable data or communication link 212. It will be understood that the data communication link 212 may include a bi-directional communication link and/or one or more dedicated uni-directional communication links.

In some examples, the sound processor 210 and the microphone 206 comprise an external portion of the cochlear implant system 200 and the implantable cochlear stimulator 214 and the electrode lead 216 comprise an implantable portion of the system 200 that is implanted within a patient's body. In alternative embodiments, one or more portions of the sound processor 210 are included within the implantable portion of the cochlear implant system 200.

The external and implantable portions of the cochlear implant system 200 may each include one or more coils configured to transmit and receive power and/or control signals via the communication link 212. For example, the external portion of the cochlear implant system 200 may include an external coil (not shown) and the implantable portion of the cochlear implant system 200 may include an implantable coil (not shown). The external coil and the implantable coil may be inductively coupled to each other, thereby allowing data to be transmitted therebetween. The data may include, for example, the magnitude and polarity of a sensed audio signal. The external coil may also transmit power from the external portion to the implantable portion of the cochlear implant system 200.

It will be noted that, in some embodiments, both the sound processor 210 and the implantable cochlear stimulator 214 may be implanted within the patient, either in the same housing or in separate housings. If the sound processor 210 and the implantable cochlear stimulator 214 are in the same housing, the communication link 212 may be realized with a direct wire connection within such housing. If the sound processor 210 and the implantable cochlear stimulator 214 are in separate housings, the communication link 212 may include one or more inductive links, for example.

Figure 3:
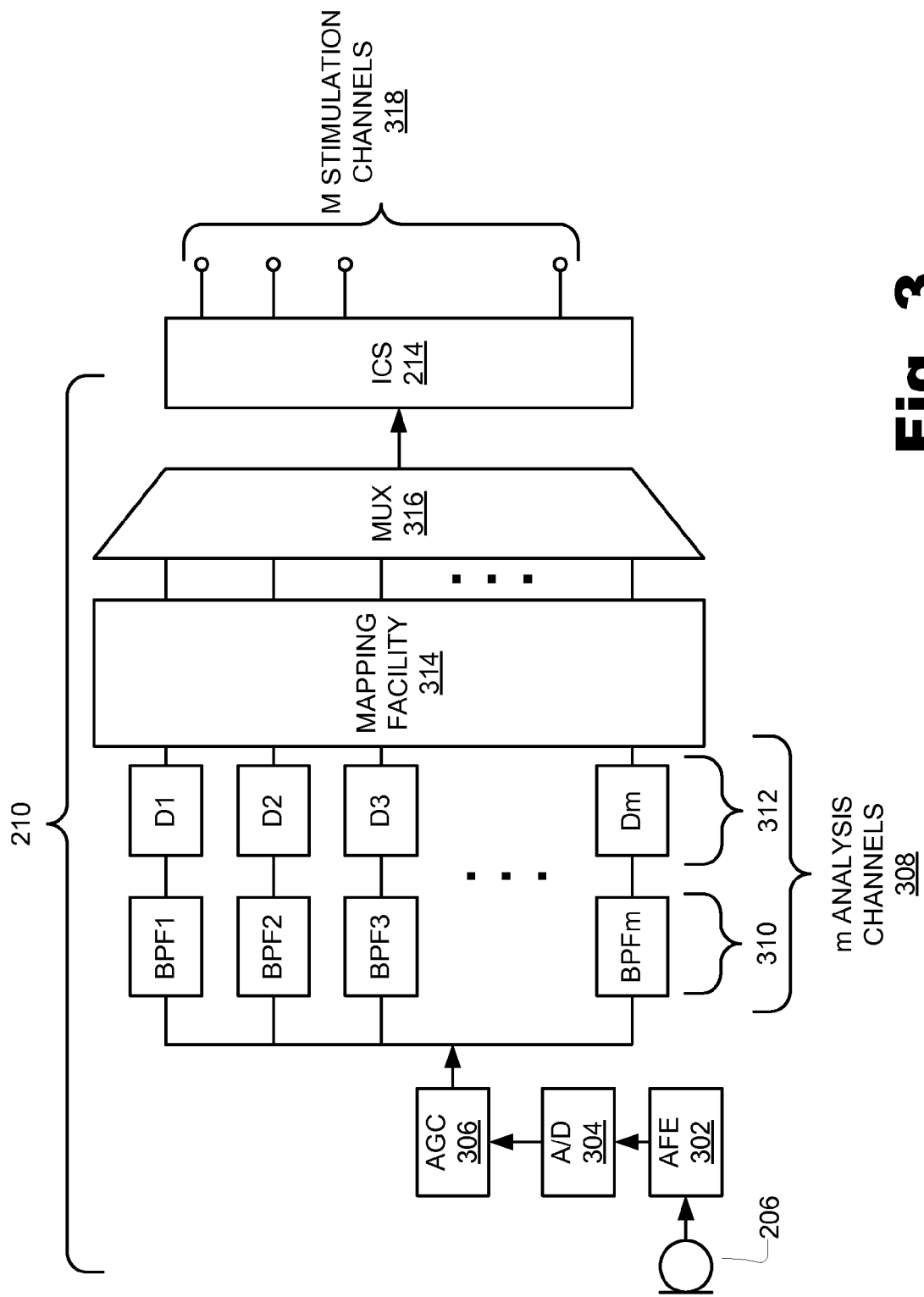
FIG. 3 is a functional block diagram of an exemplary sound processor and implantable cochlear stimulator according to principles described herein.

FIG. 3 is a functional block diagram of an exemplary sound processor 210 and implantable cochlear stimulator 214. The functions shown in FIG. 3 are merely representative of the many different functions that may be performed by the sound processor 210 and/or the implantable cochlear stimulator 214.

As shown in FIG. 3, the microphone 206 senses an audio signal, such as speech or music, and converts the audio signal into one or more electrical signals. These signals are then amplified in audio front-end (AFE) circuitry 302. The amplified audio signal is then converted to a digital signal by an analog-to-digital (A/D) converter 304. The resulting digital signal is then subjected to automatic gain control using a suitable automatic gain control (AGC) function 306.

After appropriate automatic gain control, the digital signal is subjected to a plurality of filters 310 (e.g., a plurality of band-pass filters). Filters 310 are configured to divide the digital signal into m analysis channels 308 each containing a signal representative of a distinct frequency portion of the audio signal sensed by microphone 206. Additional or alternative components may be used to divide the signal into the analysis channels 308 as may serve a particular application. For example, as described previously, one or more components may be included within sound processor 210 that are configured to apply a Discrete Fourier Transform to the audio signal and then divide the resulting frequency bins into the analysis channels 308.

As shown in FIG. 3, the signals within each analysis channel 308 may be input into an energy detector 312. Each energy detector 312 may include any combination of circuitry configured to detect an amount of energy contained within each of the signals within the analysis channels 308. For example, each energy detector 312 may include a rectification circuit followed by an integrator circuit.

After energy detection, the signals within each of the m analysis channels 308 are forwarded to a mapping facility 314. The mapping facility 314 is configured to map the signals in each of the m analysis channels 308 to one or more of M stimulation channels 318. In other words, the information contained in the m analysis channels 308 is used to define the stimulation current pulses that are applied to the patient by the implantable cochlear stimulator 214 via the M stimulation channels 318. Groups of one or more individual electrodes 218 may make up the M stimulation channels 318.

In some examples, the mapped signals are serialized by a multiplexer 316 and transmitted to the implantable cochlear stimulator 214. The implantable cochlear stimulator 214 may then apply stimulation current via one or more of the M stimulation channels 318 to one or more stimulation sites 104 within the duct of the patient's cochlea. As used herein, the term "stimulation site" will be used to refer to a target area or location to which the stimulation current is applied. For example, a stimulation site may refer to one of the locations 104 shown in FIG. 1. Through appropriate weighting and sharing of currents between the electrodes 218, as discussed in more detail below, stimulation current may be applied to any stimulation site within the cochlea 100.

As mentioned, an audio signal may include fine structure information. As used herein, "fine structure information" includes information contained in a waveform of a signal other than the envelope of the signal, and may be represented by relatively fast amplitude fluctuations in the waveform. Fine structure information facilitates the perception of musical pitch and/or voice pitch and may also include cues for spatial location for the origination of the audio signal.

Fine structure information may be present in all frequency bands of an audio signal, but is most salient in the low frequencies (e.g., less than 250 Hertz ("Hz")). However, many cochlear implant systems do not adequately convey information contained within this frequency range.

Hence, the systems and methods described herein facilitate conveyance of fine structure information to a cochlear implant patient by presenting the fine structure information to the patient via a stimulation channel 318 that is isolated from the other stimulation channels 318. In this manner, as will be described in more detail below, the effects of channel interaction may be mitigated.

Figure 4:
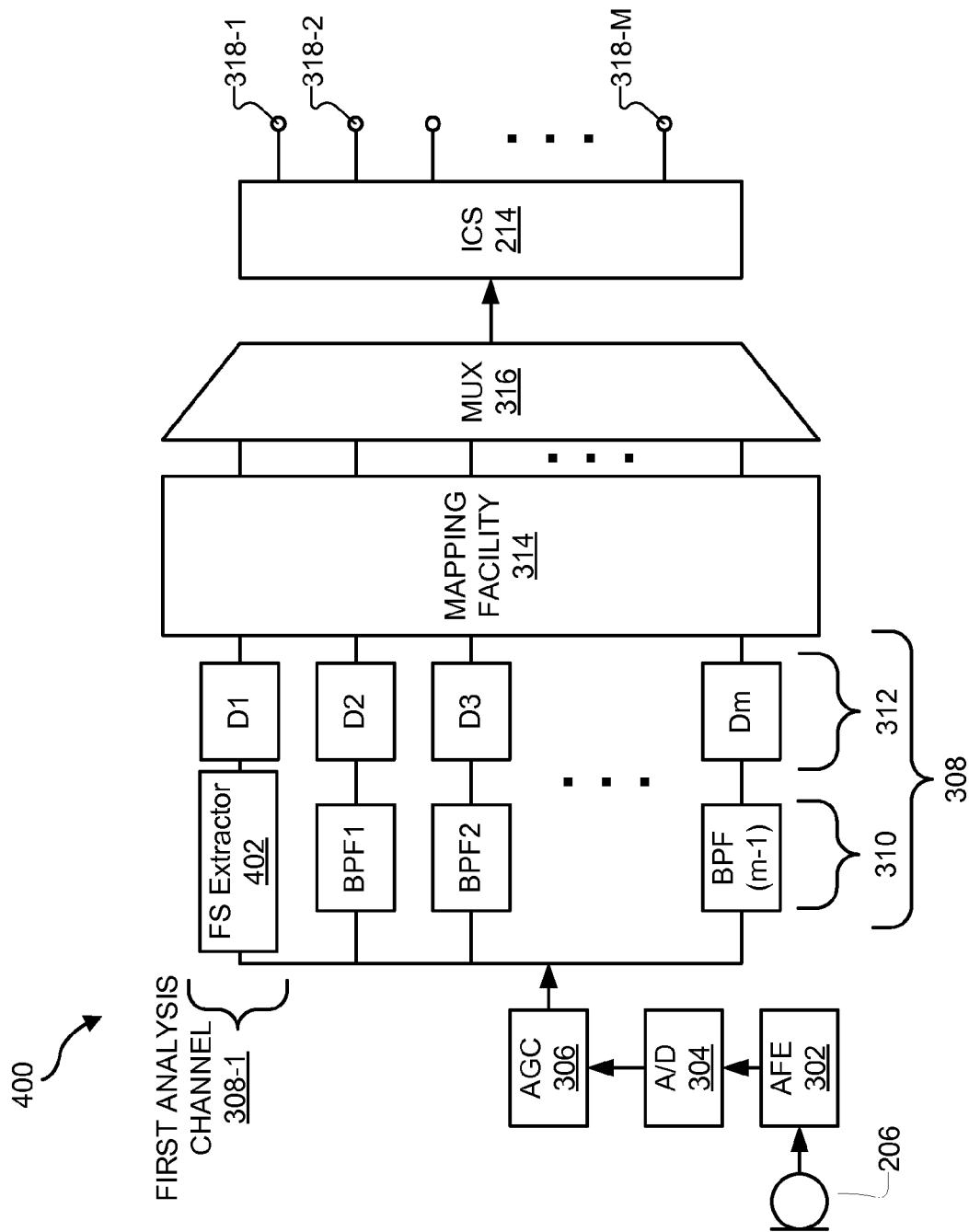
FIG. 4 illustrates an exemplary embodiment of the cochlear implant system wherein the system is configured to present fine structure information to a patient via an isolated stimulation channel according to principles described herein.

FIG. 4 illustrates an exemplary implementation 400 of the cochlear implant system 200 of FIG. 2 wherein system 200 is configured to present fine structure information to a patient via a stimulation channel (e.g., stimulation channel 318-1) that is isolated from the other stimulation channels (e.g., stimulation channels 318-2 through 318-M). Stimulation channels 318-1 through 318-M will be collectively referred to herein as "stimulation channels 318."

In some examples, a first analysis channel 308-1 within the sound processor 210 may correspond to a relatively low frequency band containing fine structure information to be presented to the patient. The low frequency band may include any range of frequencies as may serve a particular application. For example, the low frequency band may include frequencies between 60 and 250 Hz.

As shown in FIG. 4, the first analysis channel 308-1 may include a fine structure extractor 402 configured to extract fine structure information from the audio signal. The fine structure extractor 402 may include, but is not limited to, a low pass filter, a band pass filter, a frequency modulated demodulator, a fundamental frequency estimator, and/or any other suitable component and may be configured to extract fine structure information from the audio signal using any suitable technique or process.

For example, the fine structure extractor 402 may be configured to low-pass filter the audio signal (e.g., from 60 to 250 Hz). Alternatively, the fine structure extractor 402 may be configured to perform Hilbert envelope detection on the audio signal, and then filter to a pitch band (e.g., 60-250 Hz). In yet another alternative embodiment, the fine structure extractor 402 may perform explicit pitch extraction from the audio signal using any suitable technique.

In some examples, a single AGC unit 306 may be used to perform gain control for each of the analysis channels 308, as shown in FIG. 4. In some alternative examples, distinct AGC units (not shown) may be used to perform gain control for each of the analysis channels 308.

Mapping facility 314 may be configured to map the contents of the first analysis channel 308-1 to a first stimulation channel 318-1. In this manner, the fine structure information may be conveyed to the patient via the first stimulation channel 318-1.

As mentioned, the first stimulation channel 318-1 may include any number of electrodes 218 as may serve a particular application. For example, the first stimulation channel 318-1 may include a single electrode 218. In this case, the housing of the implantable cochlear stimulator 214 may serve as an indifferent electrode. Alternatively, the first stimulation channel 318-1 may include two or more electrodes 218.

In some examples, channel interaction may inhibit the ability of a patient to perceive the fine structure information applied via the first stimulation channel 318-1. As used herein, "channel interaction" refers to a situation wherein electrical stimulation applied via one stimulation channel or electrode at least in part masks the electrical stimulation applied via another stimulation channel or electrode. For example, electrical stimulation applied via a stimulation channel adjacent to the first stimulation channel 318-1 (e.g., second stimulation channel 318-2 shown in FIG. 4) may mask or interfere with the electrical stimulation applied via the first stimulation channel 318-1, thus inhibiting the ability of the patient to perceive the fine structure information applied via the first stimulation channel 318-1.

To overcome the effects of channel interaction, the cochlear implant system 100 may be configured to at least partially "isolate" the first stimulation channel 318-1 from the rest of the stimulation channels 318. As used herein, channel "isolation" may refer to any stimulation strategy or configuration configured to decrease or eliminate masking of the first stimulation channel 318-1 by one or more of the other stimulation channels 318. As will be described in more detail below, a number of different stimulation strategies and/or configurations may be used to achieve channel isolation.

Figure 5:
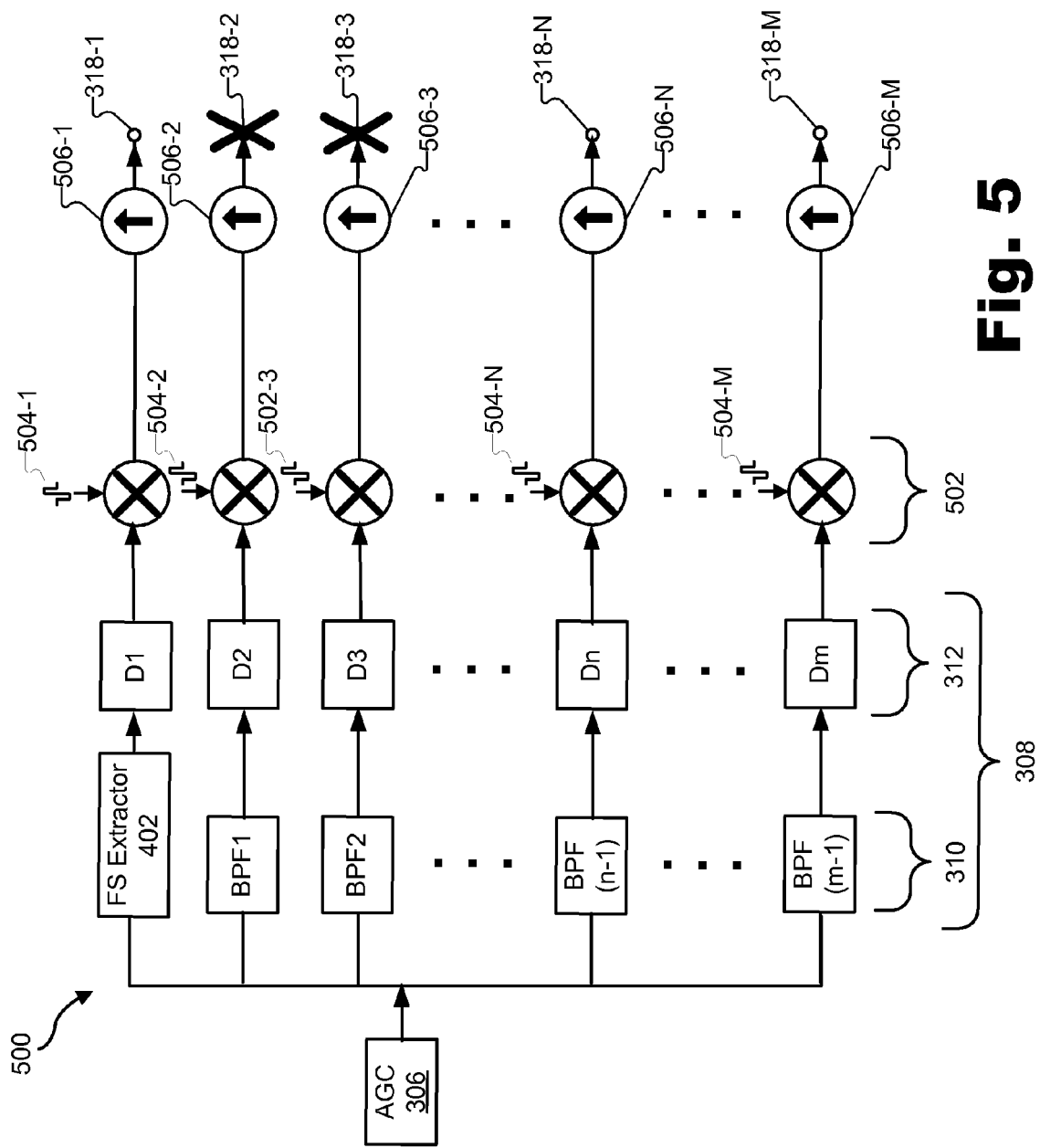
FIG. 5 is a functional block diagram of an exemplary stimulation strategy configured to isolate a stimulation channel according to principles described herein.

FIG. 5 is a functional block diagram of a first exemplary stimulation strategy 500 configured to isolate the first stimulation channel 318-1 from the rest of the stimulation channels 318-2 through 318-M. The components shown in FIG. 5 are exemplary only. Additional or alternative components may also be configured to perform the functions shown in FIG. 5. Moreover, the components may be included within the sound processor 210 and/or implantable cochlear stimulator 214 as may serve a particular application.

As depicted in FIG. 5, one or more multipliers (e.g., multipliers 502-1 though 510-M, collectively referred to herein as "multipliers 502") may be configured to multiply the signals generated by each of the analysis channels 308 with one or more carrier pulses (e.g., carrier pulses 504-1 through 504-M, collectively referred to herein as "carrier pulses 504") to generate stimulation parameters defining pulses of electrical stimulation that are to be generated by current sources 506 (e.g., current sources 506-1 through 506-M) delivered via each of the stimulation channels 318.

In some examples, the implantable cochlear stimulator 214 may be configured to deactivate one or more stimulation channels 318 adjacent to and/or near the first stimulation channel 318-1 in order to at least partially isolate the first stimulation channel 318-1 from the rest of the stimulation channels 318. For example, FIG. 5 shows the second stimulation channel 318-2, the third stimulation channel 318-3, and additional stimulation channels 318 up to, but not including, a $N^{th}$ stimulation channel 318-N as deactivated. It will be recognized that any number of stimulation channels 318 may be deactivated as may serve a particular application.

The implantable cochlear stimulator 214 may be configured to deactivate a particular stimulation channel 318 by deactivating the electrode(s) 218 that make up the stimulation channel 318, preventing current from being applied via the stimulation channel 318, deactivating a current source 506 that corresponds to the stimulation channel 318, and/or by using any other suitable procedure. Hence, deactivation of one or more channels 318 adjacent to the first stimulation channel 318-1 may be configured to at least partially isolate the first stimulation channel 318-1 by preventing the adjacent channels 318 from delivering stimulation current that masks or interferes with the stimulation current applied via the first stimulation channel 318-1.

In some examples, the implantable cochlear stimulator 214 includes deactivation circuitry configured to deactivate one or more stimulation channels 318. The deactivation circuitry may be configured to deactivate one or more stimulation channels 318 in response to fine structure information being conveyed within a particular analysis channel (e.g., the first analysis channel 318-1). The deactivation circuitry may include any combination of hardware and/or software as may serve a particular application. In some examples, the frequencies assigned to a particular stimulation channel 318 that is deactivated may be reassigned to one or more adjacent stimulation channels. To this end, the band pass filter 310 and the energy detector 312 corresponding to a deactivated stimulation channel 318 may be bypassed.

In some examples, the carrier pulses 504 with which the signals generated by each of the analysis channels 308 are multiplied may be out of phase with one another. Out of phase carrier pulses 504 may be further configured to isolate the first stimulation channel 318-1 from the rest of the stimulation channels 318 by mitigating the masking effect that the other stimulation channels may have on the first stimulation channel 318-1.

Figure 6:
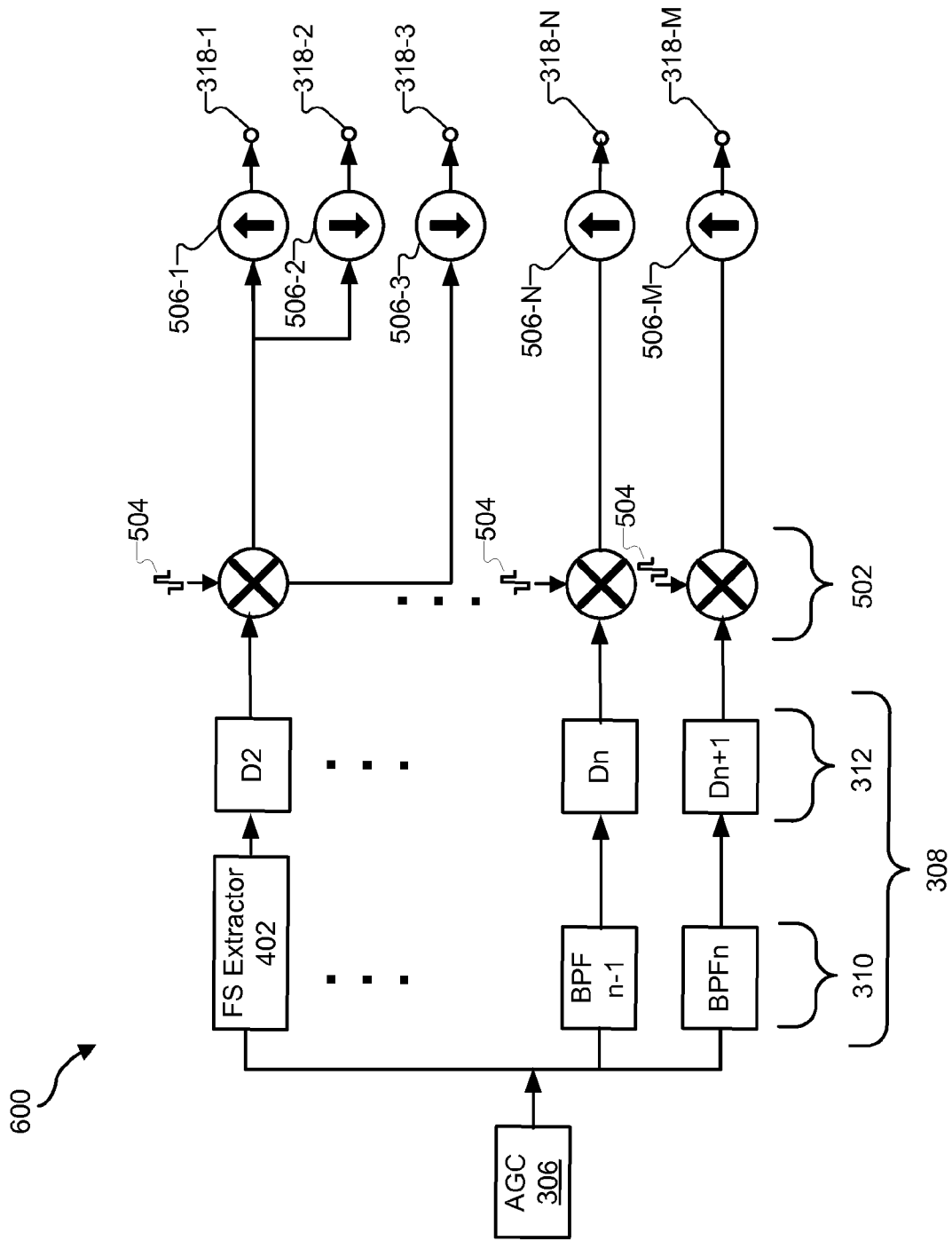
FIG. 6 is a functional block diagram of another exemplary stimulation strategy configured to isolate a stimulation channel according to principles described herein.

FIG. 6 is a functional block diagram of another exemplary stimulation strategy 600 configured to at least partially isolate the first stimulation channel 318-1 from the rest of the stimulation channels 318-2 through 318-M. The stimulation strategy depicted in FIG. 6 is configured to use current steering to isolate the current field generated by the first stimulation channel 318-1 from the current fields generated by the other stimulation channels 318.

To achieve current steering, compensating current in either direction may be applied via one or more stimulation channels 318 (e.g., stimulation channels 318-2 and 318-3) that are adjacent to the first stimulation channel 318-1. These adjacent channels 318-2 and 318-3 to which compensating current is applied may be referred to as "compensating stimulation channels." The electrodes 218 that form the compensating stimulation channels may be referred to as "compensating electrodes." It will be recognized that any number of compensating electrodes may be used as may serve a particular application.

In some examples, the compensating current is equal to a fraction of the stimulation current applied via the first stimulation channel 318-1. Moreover, the compensating current may be out of phase in relation to the stimulation current applied via the first stimulation channel 318-1.

In some examples, the compensating current serves to steer the spatial excitation field generated by the first stimulation channel 318-1 away from the spatial excitation fields generated by the other stimulation channels 318. In this manner, the effects of signal masking and channel interaction may be mitigated. In addition, the current steering may serve to effectively lower the pitch of the first stimulation channel 318-1.

To facilitate current steering, the implantable cochlear stimulator 214 may include compensation circuitry configured to select one or more electrodes 218 to serve as compensating electrodes 602 and to generate the compensating current that is applied via the compensating electrodes 602. The compensation circuitry may include any combination of hardware and/or software as may serve a particular application.

Figure 7:
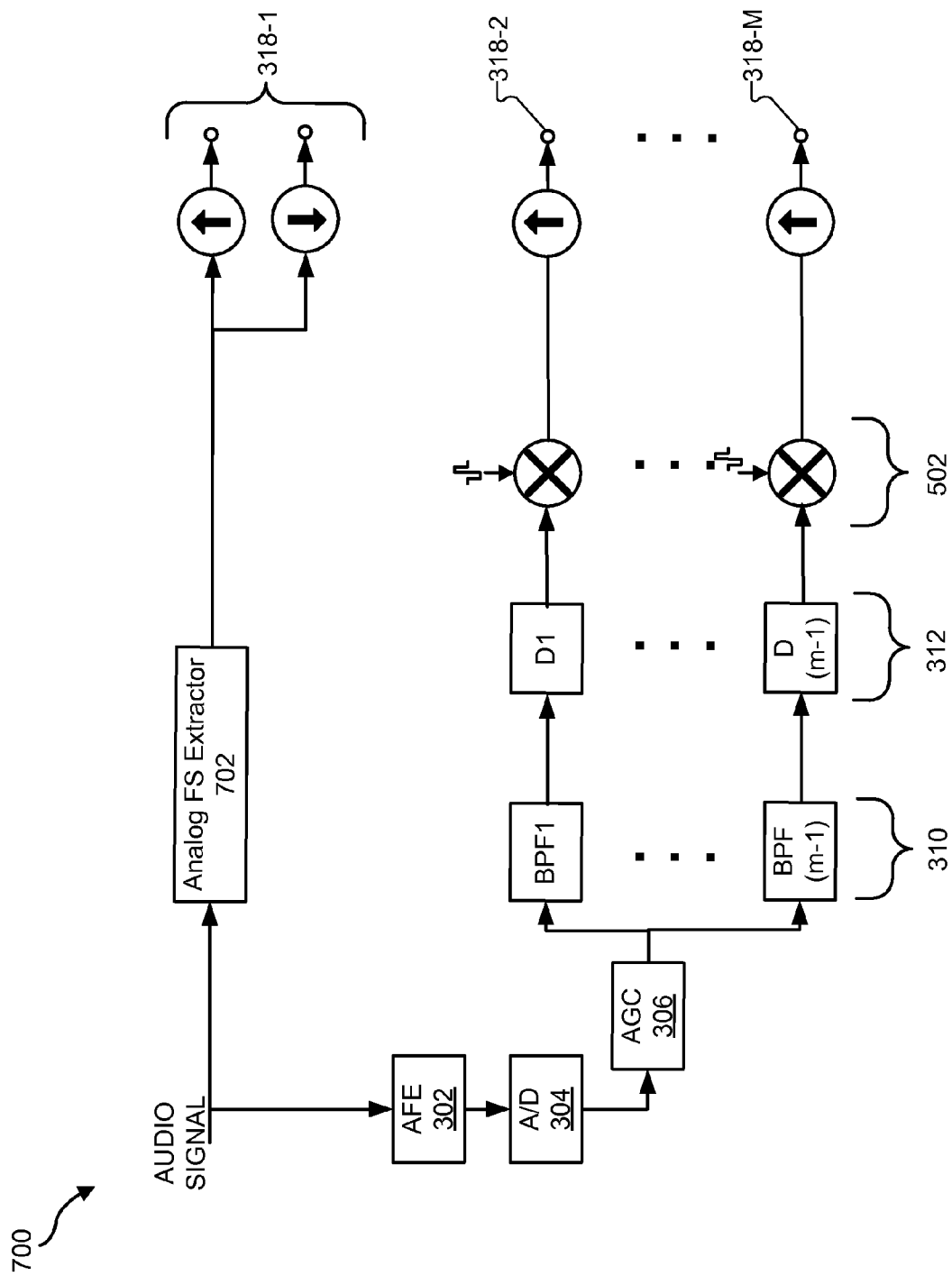
FIG. 7 is a functional block diagram of another exemplary stimulation strategy configured to isolate a stimulation channel according to principles described herein.

In some examples, it may be desirable for an analog channel to convey fine structure information to a cochlear implant patient. To this end, FIG. 7 illustrates an exemplary configuration 700 wherein the first stimulation channel 318-1 is analog. As shown in FIG. 7, the analog channel 318-1 may include an analog fine structure extractor 702 configured to extract fine structure information from the audio signal. The analog fine structure extractor 702 may include, but is not limited to, an analog filter and/or any other combination of analog circuitry configured to extract fine structure information from the audio signal.

As shown in FIG. 7, the extracted fine structure information may be conveyed to the patient via one or more electrodes that make up the first stimulation channel 318-1. Channel deactivation, current steering and/or any other isolation technique may be used to at least partially isolate the stimulation channel 318-1 from the other stimulation channels 318, which may be analog or digital as may serve a particular application.

Figure 8:
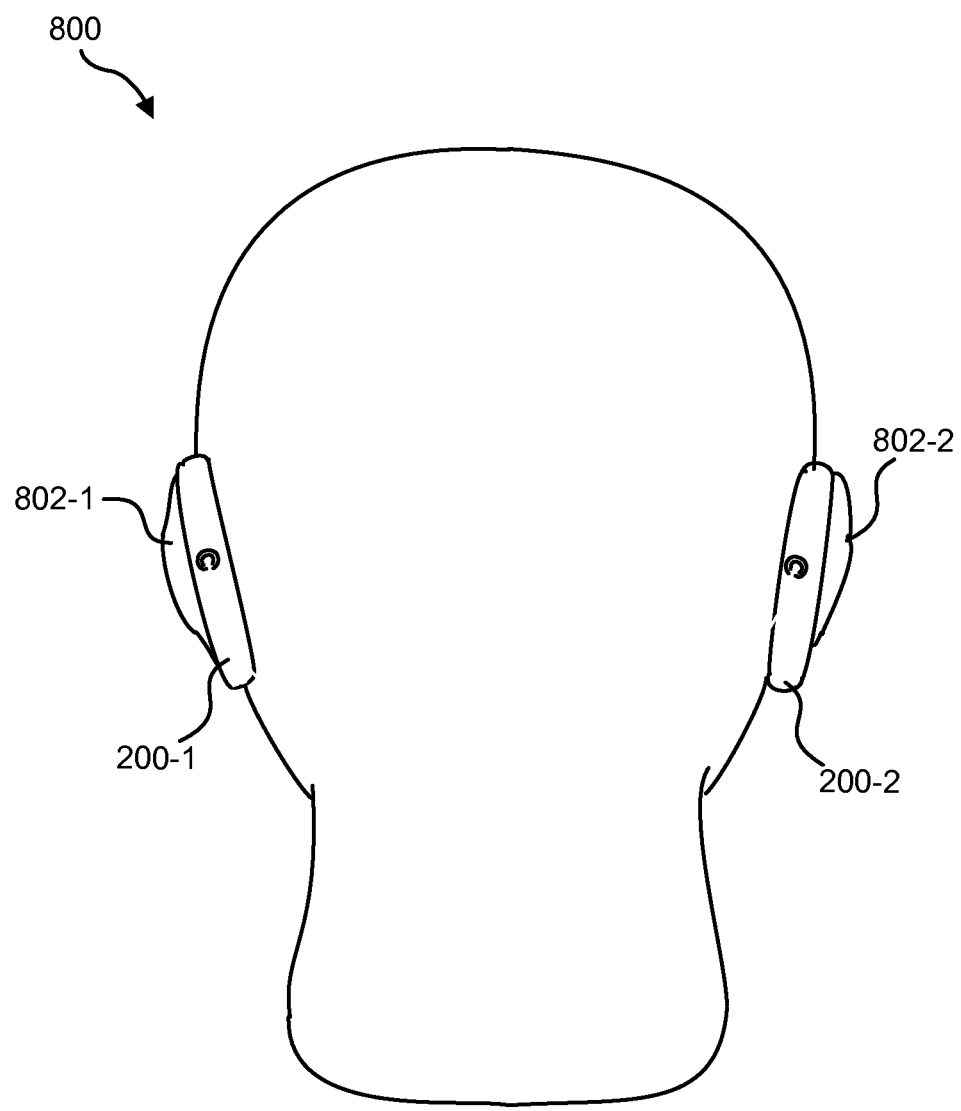
FIG. 8 illustrates another exemplary configuration configured to isolate a stimulation channel according to principles described herein.

FIG. 8 illustrates another exemplary configuration 800 configured to isolate the first stimulation channel 318-1 from the rest of the stimulation channels 318-2 through 318-M. As shown in FIG. 8, a patient may be fitted with two cochlear implant systems 200-1 and 200-2. The first cochlear implant system 200-1 corresponds to a first ear 802-1 of the patient and the second cochlear implant system 200-2 corresponds to a second ear 802-2 of the patient. It will be recognized that a single sound processor 210 may alternatively be used for both ears 802. However, for illustrative purposes, it will be assumed that a separate sound processor 210 is used for each ear 802.

In some examples, the first cochlear implant system 200-1 is configured to convey fine structure information contained within an input audio signal to the cochlea within the first ear 802-1 via a first stimulation channel 318-1. The second cochlear implant system 200-2 is configured to convey the rest of the information contained within the audio signal to the cochlea within the second ear 802-2 via one or more additional stimulation channels 318. In this manner, the first stimulation channel 318-1 may be at least partially isolated from the other stimulation channels 318. In situations wherein the patient has some residual hearing, the first cochlear implant system 200-1 may be substituted with an amplifying hearing aid.

Figure 9:
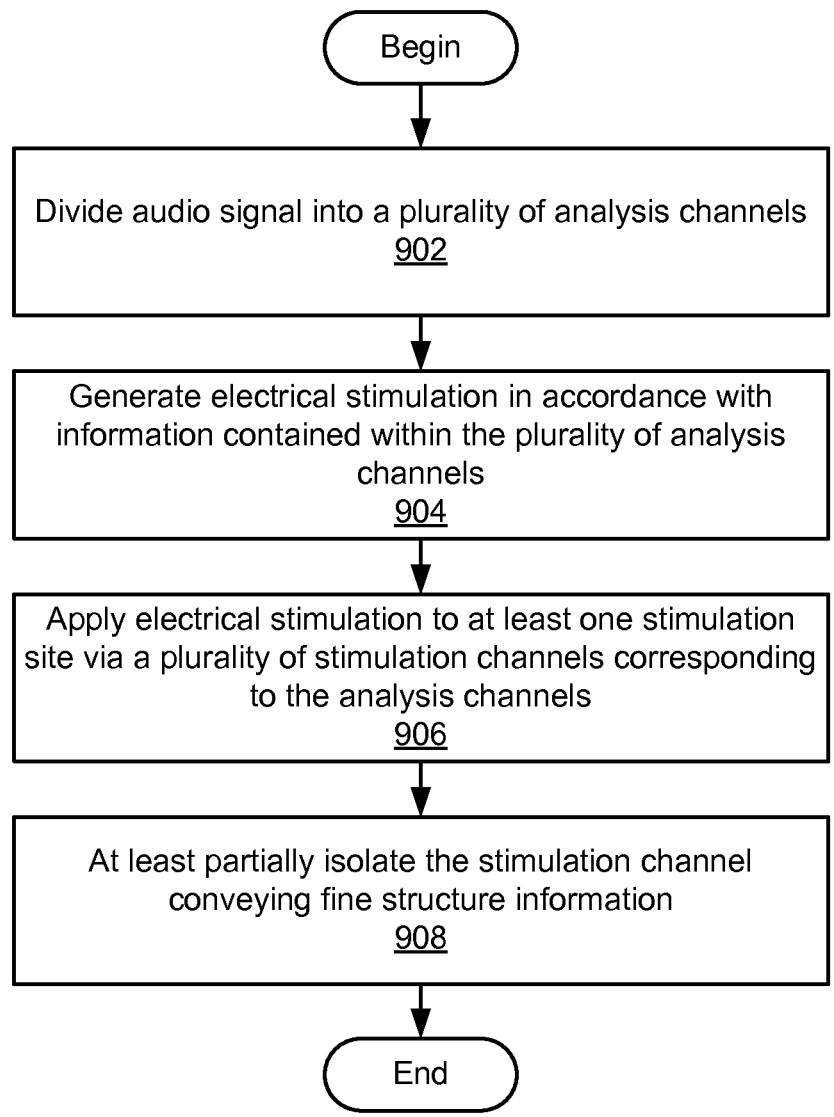
FIG. 9 illustrates an exemplary method of isolating fine structure information for a cochlear implant patient according to principles described herein.

FIG. 9 illustrates an exemplary method of isolating fine structure information for a cochlear implant patient. While FIG. 9 illustrates exemplary steps according to one embodiment, other embodiments may omit, add to, reorder, and/or modify any of the steps shown in FIG. 9. Any of the steps described in FIG. 9 may be performed by sound processor 210, implantable cochlear stimulator 214, and/or any other component included within cochlear implant system 200 as may serve a particular application.

In step 902, an audio signal is divided into a plurality of analysis channels. Each of the analysis channels contains information corresponding to a distinct frequency band of the audio signal, and one of the analysis channels contains fine structure information. The audio signal may be divided into a plurality of analysis channels in any of the ways described herein.

In step 904, electrical stimulation is generated in accordance with the information contained within the plurality of analysis channels. The electrical stimulation may be generated in any of the ways described herein.

In step 906, the electrical stimulation is applied to at least one stimulation site within a patient via a plurality of stimulation channels. Each stimulation channel corresponds to a particular analysis channel and may include any number of electrodes. The electrical stimulation may be applied in any of the ways described herein.

In step 908, the stimulation channel conveying fine structure information is at least partially isolated from the rest of the stimulation channels. The isolation may be realized using any of the stimulation strategies described herein.

As detailed above, the methods and systems described herein facilitate conveyance of fine structure information to a cochlear implant patient. As an example, an exemplary method includes dividing an audio signal into a plurality of analysis channels corresponding to distinct frequency bands, with one of the analysis channels containing fine structure information corresponding to the audio signal. The method further includes generating electrical stimulation in accordance with information within each of the analysis channels and applying the electrical stimulation to at least one stimulation site within a patient via a plurality of stimulation channels corresponding to the analysis channels. The method further includes at least partially isolating the stimulation channel conveying fine structure information from the rest of the stimulation channels.

An exemplary system includes a sound processor configured to divide an audio signal into a plurality of analysis channels corresponding to distinct frequency bands, with one of the analysis channels containing fine structure information corresponding to the audio signal. The system further includes an implantable cochlear stimulator communicatively coupled to the sound processor and configured to generate electrical stimulation in accordance with information contained within the analysis channels, apply the electrical stimulation to at least one stimulation site within a patient via a plurality of stimulation channels corresponding to the analysis channels, and at least partially isolate the stimulation channel conveying fine structure information from the rest of the stimulation channels.

Another exemplary system includes a sound processor configured to divide an audio signal into a plurality of analysis channels, wherein each of the analysis channels contains information corresponding to a distinct frequency band of the audio signal, and wherein one of the analysis channels contains fine structure information corresponding to the audio signal. The system further includes first electrical circuitry configured to generate electrical stimulation in accordance with information contained within each of a plurality of analysis channels and second electrical circuitry configured to apply the electrical stimulation to at least one stimulation site within a patient via a plurality of stimulation channels. Each of the stimulation channels corresponds to one of the analysis channels and is configured to convey the information contained within the analysis channel to the patient. For example, one of the stimulation channels is configured to convey the fine structure information to the patient. In some examples, the second electrical circuitry is further configured to at least partially isolate the stimulation channel configured to convey the fine structure information the rest of the stimulation channels.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
dividing, by a sound processor, an audio signal presented to a patient into a plurality of analysis channels, wherein each of the analysis channels contains information corresponding to a distinct frequency band of the audio signal, and wherein a first analysis channel included in the plurality of analysis channels contains fine structure information corresponding to the audio signal;

determining, by the sound processor, that a first stimulation channel included in a plurality of stimulation channels made up by a plurality of electrodes implanted within the patient corresponds to the first analysis channel and is configured to convey the fine structure information to the patient;

at least partially isolating, by the sound processor, the first stimulation channel from a rest of the stimulation channels by deactivating at least one stimulation channel included in the plurality of stimulation channels and adjacent to the first stimulation channel, reassigning frequencies associated with the deactivated at least one stimulation channel to one or more other stimulation channels included in the plurality of stimulation channels, and directing an implantable cochlear stimulator to apply electrical stimulation representative of the fine structure information to the patient by way of the first stimulation channel while the at least one stimulation channel is deactivated.

2. The method of claim 1, wherein the frequency band corresponding to the analysis channel containing the fine structure information comprises a range of frequencies relatively lower than a range of frequencies corresponding to a rest of the analysis channels.

3. The method of claim 2, wherein the frequency band corresponding to the analysis channel containing the fine structure information comprises frequencies that are substantially less than or equal to 250 Hertz.

4. The method of claim 1, wherein the deactivating of the at least one stimulation channel comprises deactivating at least one electrode that makes up the at least one stimulation channel.

5. The method of claim 1, wherein the first stimulation channel is analog.

* * * * *